(12) United States Patent
Kawasaki

(10) Patent No.: US 7,161,677 B2
(45) Date of Patent: Jan. 9, 2007

(54) CONDENSATION SENSOR AND METHOD OF CONTROLLING CONDENSATE FILM IN SEALED SPACE WITH CONDENSATION SENSOR

(75) Inventor: Koji Kawasaki, Nagoya (JP)

(73) Assignee: Airex Co., Ltd., Aichi (JP)

( * ) Notice: Subject to any disclaimer, the term of this patent is extended or adjusted under 35 U.S.C. 154(b) by 32 days.

(21) Appl. No.: 10/990,354

(22) Filed: Nov. 15, 2004

(65) Prior Publication Data

US 2005/0111003 A1    May 26, 2005

Related U.S. Application Data

(63) Continuation of application No. PCT/JP03/05646, filed on May 6, 2003.

(30) Foreign Application Priority Data

May 14, 2002    (JP) ............... 2002-138575

(51) Int. Cl.
    *G01N 21/00*    (2006.01)
(52) U.S. Cl. ................ 356/437; 250/339.13
(58) Field of Classification Search ........ 356/432–440; 250/339.01, 339.06, 339.12, 339.13
    See application file for complete search history.

(56) References Cited

U.S. PATENT DOCUMENTS

| | | | | |
|---|---|---|---|---|
| 4,661,320 A | * | 4/1987 | Ito et al. ..................... | 422/86 |
| 4,701,052 A | * | 10/1987 | Schoen, Jr. ................ | 356/369 |
| 5,691,465 A | * | 11/1997 | Carr et al. .................. | 73/24.02 |
| 6,141,088 A | * | 10/2000 | Beysens et al. ............ | 356/72 |
| 6,230,545 B1 | * | 5/2001 | Adolph et al. ............. | 73/31.05 |
| 6,897,960 B1 | * | 5/2005 | DiMeo et al. .............. | 356/437 |

FOREIGN PATENT DOCUMENTS

| | | |
|---|---|---|
| JP | 57-173778 | 10/1982 |
| JP | 11-230899 | 8/1999 |
| WO | WO-00/74734 A1 | 12/2000 |
| WO | WO-01/71321 A1 | 9/2001 |

OTHER PUBLICATIONS

International Search Report in Japanese for PCT/JP03/05646 mailed Aug. 26, 2003.
Patent Abstracts of Japan for JP11-230899 published Aug. 27, 1999.
Patent Abstracts of Japan for JP57-173778 published Oct. 26, 1982.

\* cited by examiner

*Primary Examiner*—Hoa Q. Pham
(74) *Attorney, Agent, or Firm*—Darby & Darby

(57) ABSTRACT

A condensation sensor detects whether hydrogen peroxide gas has condensed in a sealed space and determines the condition of a condensate film upon passage of time. The condensate film in the sealed space is controlled with the condensation sensor. The condensation sensor includes a condensate forming part with a plurality of glass plates arranged so that a direction of irradiation is substantially perpendicular to a surface direction, and the condensate forming part is disposed between a projector and a light receiver. The condensation sensor is placed inside an isolator and irradiated with laser beams. The condensate film formed on the glass plates is detected from a change in the quantity of light received by the light receiver, thus the condition of condensation on the surface of an item to be sterilized inside the isolator is presumed, and accordingly, the necessary and sufficient amount of gas introduced is determined.

20 Claims, 15 Drawing Sheets

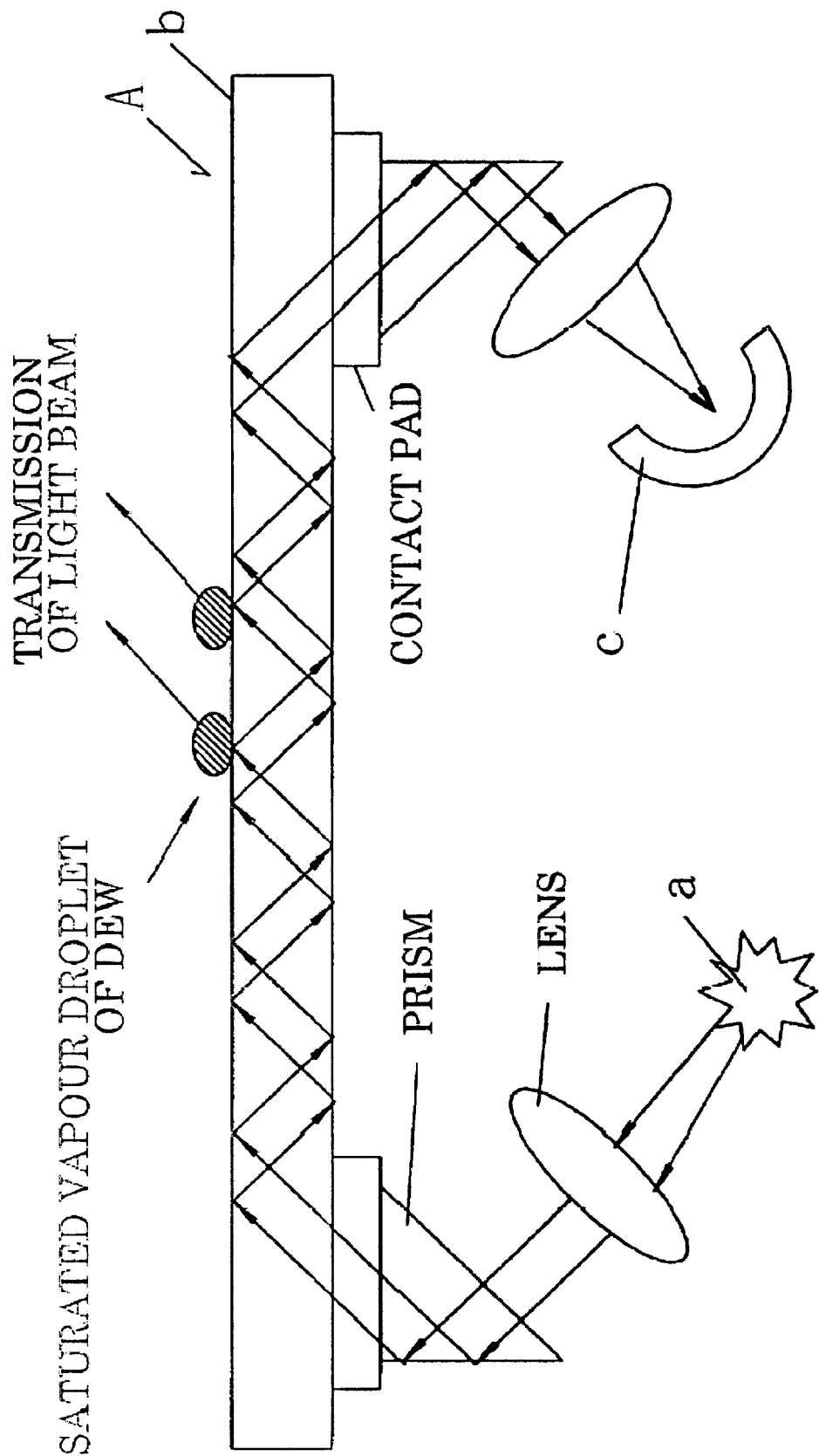

US 7,161,677 B2

CONDENSATION SENSOR AND METHOD OF CONTROLLING CONDENSATE FILM IN SEALED SPACE WITH CONDENSATION SENSOR

CROSS-REFERENCE TO RELATED APPLICATION

This application is a Continuation of International Patent Application Ser. No. PCT/JP03/05646 filed May 20, 2003, which was published in Japanese on Nov. 20, 2003 as WO 03/095994 A1, and claims priority of Japanese Patent Application No. 2002-138575 filed on May 14, 2002 both of which are incorporated herein by reference in their entireties.

BACKGROUND

1. Field of the Invention

This invention relates to a condensation sensor which detects the existence of a condensate film of gas inside a sealed space where a gas for decontamination is supplied. The condensate film of gas is formed on the inside surface of the sealed space or on an object inside the space. The invention also relates to a method of controlling the condensate film inside the sealed space with the condensation sensor.

2. Description of the Prior Art

In manufacturing processes, such as for medical supplies and food, an operation in a sterilized condition is indispensable. Decontamination management inside a sealed space where a decontamination operation is performed needs to be carried out correctly and strictly. In the structure which supplies the gas for decontamination to the sealed space and decontaminates the inside of the sealed space, it has been known in recent years that there is a close relationship between the condensation phenomenon of the gas for decontamination inside the sealed space and the change of the number of residual bacilli on the surface of a decontamination subject inside the sealed space. Since it is very important to know when the supplied gas for decontamination begins to condense in the sealed space, a condensation sensor is provided for detecting when condensation starts.

FIG. 11 illustrates a condensation sensor (A) with a conventional structure, as disclosed in FIGS. 1–3 of International Publication No. PCT/WO01/71321, which is equipped with a light source (a) which emits light of predetermined wavelength, a glass window (b) of fixed thickness and a light sensor (c) which measures the amount of light emerging from the window (b). As shown in FIGS. 12a and 12b, the upper surface of the glass window (b) of the condensation sensor (A) faces inside a sealed space (D) where the gas for decontamination is supplied. On the other hand, the undersurface side of the glass window (b) is fixed to the surface of a wall of the sealed space (D) facing away from the sealed space (D). In this structure, a light from the light source (a) emerges into a right angled prism (FIG. 11) from the undersurface side of the glass window (b) as shown in FIG. 11. The light sensor (c) detects the light which penetrates the inside of the glass window (b) and measures the amount of light.

In this structure, if the gas saturates inside the sealed space after supplying the gas for decontamination inside the sealed space (D), a condensation phenomenon happens on the upper side of the glass window (b) facing the sealed space (D) and a condensation film is formed on the glass window (b). In this state, light emitted from the light source (a) repeatedly passes through the inside of the glass window (b) and reflects. Light irradiated out of the glass window (b) escapes and is scattered about in the plane of the condensation film bordering the glass window (b). For this reason, the intensity of a beam measured by the light sensor (c) decreases compared to when there is no condensation. By using such a phenomenon, a condensation start time of a condensation state of the gas for decontamination on the surface of the decontamination subject inside the sealed space (D) can be determined by changing the amount of light with the condensation sensor (A).

However, the structure of the decontamination subject is usually very complicated and not a plane like the glass window of the above-mentioned condensation sensor. Then, it is possible to have a portion on which the gas for decontamination cannot spread easily, i.e., a so-called cold spot. Therefore, there is a problem so that it cannot be presumed simply that a condensation state of the gas for decontamination on the glass window of the above-mentioned condensation sensor is in the condensation state on a surface of the decontamination subject. For this reason, even if a condensation sensor detects that condensation has occurred, the gas for decontamination in many cases is supplied superfluously or the decontamination subject may have an imperfect decontamination portion. Cost increases due to the increases in the decontamination time and aeration time, and there is also a possibility that the decontamination subject might corrode.

Since, in this composition, the light which passes through the glass window is scattered at the plane of the condensate film bordering the glass window, although this composition is detectable when the gas for decontamination condenses on the glass window surface, it is difficult to determine the mode of a subsequent condensate film correctly and in detail with respect to time. Also, since the upper surface of the glass window (b) needs to face the sealed space (D), as shown in FIGS. 12a and 12b, the installation is restricted because the condensation sensor (A) has to be disposed on the surface of a wall of the sealed space (D). Although a predetermined box (E) is proposed in which the condensation sensor (A) is fixed to the surface of a wall of the sealed space (D) detachably in order to secure convenience, it will be necessary to have a fan (c) and a larger size in order to circulate the air in box (E). Thus, the equipment is complicated. There are also problems in attracting disturbances, and exact detection is difficult to obtain.

Furthermore, since a light emerges inside a glass window of the conventional condensation sensor and the detected light repeatedly reflects inside the glass window, in order to acquire exact information, the length and thickness of the glass window must be determined to some extent (for example, a full length of the glass window is about 20 cm and the window thickness is about 1 cm). Therefore, there is a limit in miniaturizing the conventional condensation sensor.

Then, this invention provides a method for managing the condensate film in the sealed space using the condensation sensor which can determine the mode of a subsequent condensate film correctly and in detail with respect to time, and this condensation sensor can solve at least one of the above-mentioned problems while it can detect whether the gas used for decontamination condenses in the sealed space.

SUMMARY OF THE INVENTION

This invention relates to a condensation sensor having one set or several sets of light transmitters which irradiate light in a certain direction from the light source, one set or several sets of photo-detectors which are attached in the position which faces the irradiation light of the light transmitters and generates a signal output corresponding to the intensity of beam measured and a condensate forming part which one sheet or several sheets of transparent plates are attached between a light source of light transmitters and photo-detector so that the above-mentioned irradiation light may be detected by the surface on which gas condenses and come to reach the glass plates with surrounding atmosphere.

The above-mentioned condensation sensor is installed into a sealed space and is used to detect the start time of the condensation of the gas supplied to this sealed space. Furthermore this condensation sensor can detect the mode of the condensation film after a condensation start with time while being able to detect the time of a condensation start correctly. In addition, the above-mentioned gas is defined as the activated gas in which the exact steam pressure characteristic is shown and mixed gas is also contained.

In this embodiment, when gas is supplied into a sealed space in which the condensation sensor is installed, gas is spread in that space. Then since the currounding atmosphere and the gap between the transparent boards of a condensation sensor are in the same atmosphere, gas infiltrates into the gap between transparent plates. If the injection of gas is continued further, the sealed space saturates and the gas condenses on the transparent plates of condensation forming part. When a light is irradiated from a light transmitters in this condition, the light will penetrate a condensation film and this penetration light is detected by the photo-detector. The intensity of beam detected with a photo-detector decreases compared with one at the time of non-condensing. This is because the light is scattered and absorbed what passed through the condensation film. And if the thickness of condensation film increases further after that, the intensity of beam of penetration light decreases further corresponding to it. That is, with this invention by carrying out the monitoring of the change of the intensity of beam by photo-detector the time of the condensation start of the supplied gas is detectable and furthermore, it becomes possible to detect also about the mode change with time on the transparent board of a subsequent condensation film.

Furthermore it becomes possible by changing the gap of the transparent plate of condensate forming part suitably to form the portion in this condensate forming part in which a gas easily tends to spread or not. For example, if the surface of object is complicated to form a condensation situation on it, the gap of transparent plate is set up in a narrow gap. Since a condensation environment of a surface of an object and a condensation sensor is common in that gas cannot permeate easily, it can make the condensation state of the gas on the object surface, and the condensation state of the gas on the transparent board of a condensate forming part approximate by changing gap. Therefore, it becomes possible to presume the condensation state of the gas on the object surface with sufficient accuracy by the information acquired with the condensation sensor.

In this embodiment since the light irradiated from the light transmitters reaches to the photo-detector after passing two or more transparent plates, the information of the intensity of light obtained by this photo-detector is the cumulative information of each transparent plate surface according to the prepared number of plates. Even if the condensation film detection on each transparent plate is difficult due to a slight thickness, it becomes possible to catch the light certainly with the photo-detector. This also reduces measurement error. As composition of the condensate forming part concerning this invention, the irradiation direction of a light and the direction of surface of a transparent plate is the composition which is not in agreement at least and the angle which mutual makes can be changed suitably.

Although sealed space is needed facing only a glass window with the conventional sensor. The embodiment of this invention may make the both sides of a transparent plate face in the sealed space, it can install the whole condensation sensor in the sealed space as it is. For this reason, while being able to install a sensor in the arbitrary places of sealed space, the information on many points can also be simultaneously acquired by installing two or more condensation sensors in one sealed space. Also, it becomes unnecessary to equip this invention with a fan like the conventional invention, it does not invite enlargement and complication of equipment, and does not have the influence by disturbance.

The condensate forming part may include the spacer of thin board by which the predetermined portion and a fixer to fix this spacer and a transparent plate and the perimeter part of the transparent plate by which a spacer is not installed is made into the opening which open each gap and currounding atmosphere between each transparent board. An alternate embodiment is that the condensate forming part include two or more transparent boards and the holding implement possessing holding slots. The end of each transparent board is inserted in a holding slot and held in parallel. The other part of transfer boards by which a holding implement is not inserted is made into the opening which open each gap and currounding atmosphere between each transparent board.

In this embodiment, two or more transparent plates are installed and the gap between transparent plates can consider a condensate forming part as currounding atmosphere and the composition which opened.

Then the composition by which the transparent plate of a condensate forming part is installed so that the direction of a field and the irradiation direction becomes almost perpendicular between a light transmitters and a photo-detector.

The irradiation light cause incident almost perpendicularly to the condensation film on a transparent plate, the reflection of the irradiation light in transparent face can be suppressed as much as possible and it becomes possible to fully secure the intensity of beam. Therefore, it is possible to detect the mode of a condensation film certainly.

Moreover, the composition of light irradiated from the light transmitters can be laser light. By adopting a laser light that the output is high and excellent in the inclination characteristic, it becomes possible to increase the number, the thickness or the interval of a transparent plate and the penetration light obtained with a photo-detector becomes the information with a more exact condensation film.

The light transmitters can be a LED (Light Emitting Diode). An embodiment of this invention equipped with the LED has an advantage of low generation of heat. Therefore, in order not to raise the temperature of the circumference of a condensation forming part, it is lost that the condensation timing detected by the condensation sensor and the condensation timing in a sterilization subject deviate. This becomes possible to presume with sufficient accuracy the condensation situation of the hydrogen peroxide gas in a sterilization subject by the detection result of a condensation sensor.

Another embodiment is the condensate forming part or the condensation sensor itself is surrounded with a breathable material. Then the surface state of the sterilization subject covered by the substance with breathable material and the surrounding environment of a condensation forming part can be made alike as much as possible. Thereby, the reliability of the information about the obtained condensation increases and it becomes possible to presume the condensation situation of the sterilization subject covered by the gas permeability substance with sufficient accuracy. The test results of biological indicator covered with the breathable material such as Tyvek sheet can be predicted by this condensation sensor.

A further embodiment is a condensate forming part or a condensation sensor itself is contained in a porous case that two or more holes for air introduction in the wall and an outlet are formed and air inhalation equipment introduces air into a case from a hole and discharges from an outlet to make an airflow. Since the air of the sealed space flows to one direction around a condensate forming part, the measurement environment is stabilized and the measurement accuracy improves. The air of the sealed space is compulsorily sent into a condensate forming part. The environment of the sealed space and the surrounding environment of a condensation forming part can be made alike as much as possible. This becomes possible to presume with sufficient accuracy the condensation situation of the hydrogen peroxide gas in a sterilization subject by the detection result of a condensation sensor.

Furthermore, a condensation film management method in the sealed space can be performed using the condensation sensor described above. That is, it is the condensation film management method in the sealed space which installs a condensation sensor in a sealed space, supplies gas to this sealed space and detects the existence of the condensation film formed on the surface of the transparent plate when gas condenses by using a change of a intensity of a beam by detecting with a photo-detector of a condensation sensor with the passage of time.

In this embodiment, if the intensity of beam detected after the gas injection decreases as compared with the intensity of beam measured before the gas injection, irradiation light is scattered about and absorbed in a condensation forming part, and it can predict that escape light arise in the condensate forming part. That is, the gas condenses on the transparent plates and the condensation film is formed. By this invention it can be detected correctly, without producing time lag from a series of experiment results rather than the method of detecting the time of a condensation start using the conventional condensation sensor.

Moreover, an embodiment using the condensation sensor of this invention and the composition whose gas supplied to the sealed space may be a gas for decontamination. As gas for decontamination, what gasified decontamination agents, such as formaldehyde, ethylene oxide, acetic peroxide solution, and ozone water, is illustrated. In addition, Chemistry T term decontamination, an asepsis, sterilization, sterilization, etc. are included in decontamination.

Then the embodiment of the condensation sensor concerning this invention is installed in the isolator with which a decontamination subject is settled and the gas for decontamination supplies into the sealed space of this isolator may be proposed. In this embodiment, if the gas for decontamination is supplied in the isolator and the inside of the isolator is in saturation, the gas for decontamination condenses on the condensate forming part of a condensation sensor. A light can detect the time of the condensation start of the gas for decontamination based on the principle that it is scattered about and absorbed with a condensation film and the intensity of beam decreases. Then it turns out that this invention can be detected correctly from a series of experiment results rather than the method of detecting the time of the condensation start of the gas for decontamination of sealed space by the conventional condensation sensor.

By the way, when presuming the condensation situation of the decontamination subject surface in the same isolator, in case that a decontamination subject is complicated form, the interval of the transparent plate of a condensation sensor is set up narrowly. This becomes possible to form temporarily the cold spot at which the gas for decontamination cannot spread easily in this condensate forming part by narrowing the gap of a transparent plate. Then this becomes possible to reproduce the condensation state of the gas for decontamination on the decontamination subject surface in the condensation state of the gas for decontamination on the transparent plate of a condensate forming part. This becomes possible to presume the condensation state of the gas for decontamination on the decontamination subject surface with sufficient accuracy from the information acquired by the condensation sensor.

As mentioned above, there is a close relation to the reduction of the number of residual bacilli of the decontamination subject surface which exists in the inside of the sealed space and this space itself and the condensation phenomenon of the gas for decontamination which happens inside the sealed space, the decontamination management of sealed space can be performed exactly with this invention. Furthermore, the embodiment using hydrogen peroxide gas as gas for decontamination is presented. The reason hydrogen peroxide gas is used is that hydrogen peroxide gas is cheap with powerful sterilization capability. Moreover, since this hydrogen peroxide gas is finally decomposed into oxygen and water, a point with little influence to environment is one of the reasons.

Furthermore, based on time change of the intensity of light detected by the photo-detector of a condensation sensor, the embodiment which detects change of thickness of the condensation film on the transparent board formed when gas condenses is presented.

Light penetrates the condensation film formed on the transparent plate and the penetration of the light is detected, in case that when the intensity of a beam decreases continuously along with time progress, it turns out that thickness of a condensation film is increasing. Moreover, if the intensity of beam becomes fixed after that, it turns out that increase of the above-mentioned thickness of film stopped and it became fixed. Since it turns out that there is a close relation to the reduction of the number of residual bacilli of the decontamination subject surface which exists in the inside of sealed space and the thickness of film of the gas for decontamination condensed inside sealed space and it is also understood that the decontamination effect does not improve any more if the thickness of film is fixed. With this embodiment the number of bacilli which remains in sealed space can be managed correctly and in detail and the thickness whose decontamination effect does not improve any more can be carried out, it becomes possible to get to know correctly the amount of injection gas required for decontamination.

Also a condensation film management method in the sealed space, include using the condensation sensor that two or more condensation sensors are installed in the sealed space. By detecting of two or more condensation situations of the sealed space at same time, the condensation situation of the gas inside the sealed space much more detailed is acquired and the reliable presumption is attained.

BRIEF DESCRIPTION OF THE DRAWINGS

The foregoing and other features of the present invention will be more readily apparent from the following detailed description and drawings of the illustrative embodiments of the invention wherein like reference numbers refer to similar elements and in which:

FIG. 11 is a diagram showing a prior art condensation sensor;

FIG. 12(*b*) is a use mode figure showing the prior art condensation sensor with box (E) outside the sealed space;

DETAILED DESCRIPTION OF THE PREFERRED EMBODIMENTS

Figure 1:
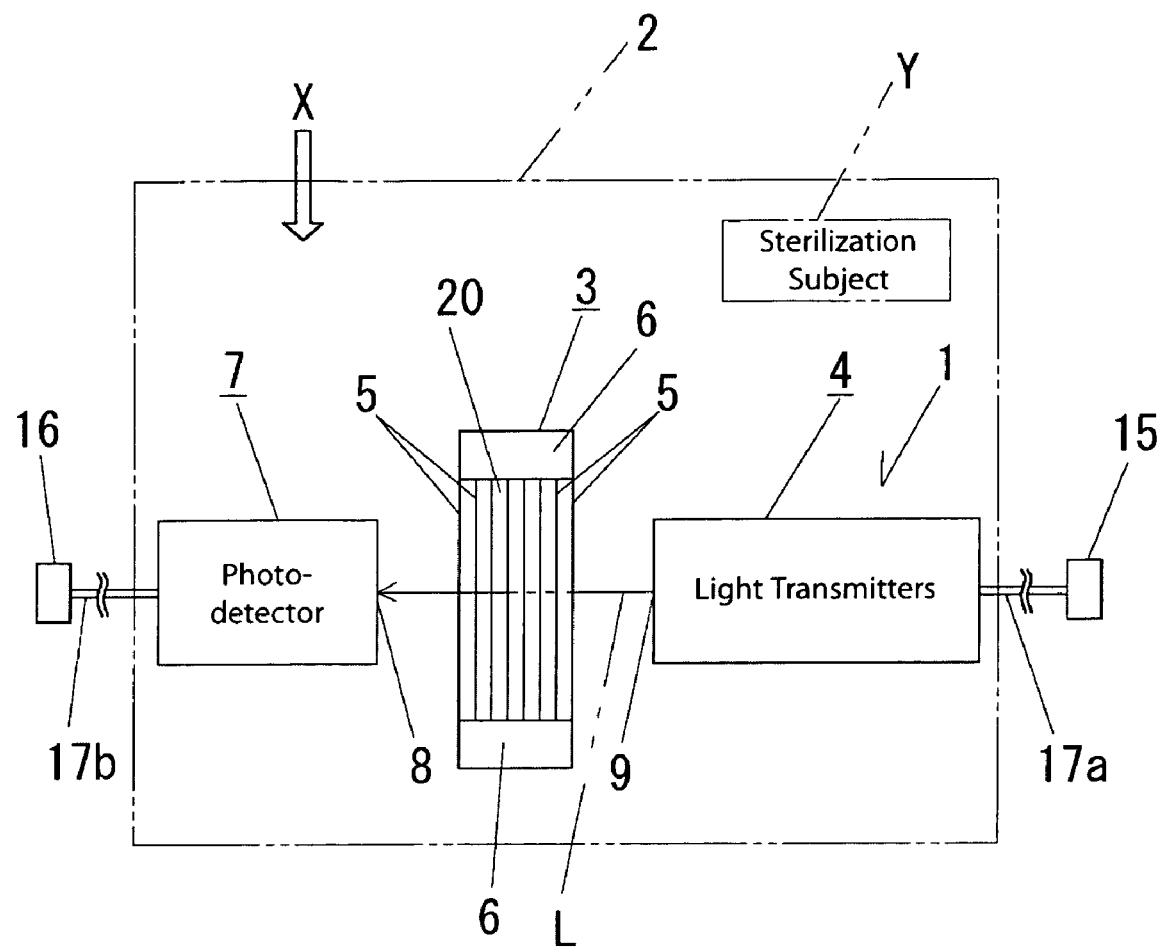
FIG. 1 is a concept diagram of the condensation sensor in accordance with the present invention.

FIG. 1 shows the main component of an apparatus in accordance with the invention of a condensation sensor (1), according to an embodiment of the present invention.

The condensation sensor (1) is equipped with a light transmitters (4), a photo-detector (7) and a condensation forming part (3) equipped between the light transmitters (4), and the photo-detector (7). The condensation sensor (1) is installed in isolator equipment (2) with which hydrogen peroxide gas (X) for sterilization is supplied. Moreover, the isolator (2) is equipped with a sterilization subject (Y). In this embodiment of the present invention, the construction of the isolator (2) is well-known. The details of this isolator (2) are omitted.

Laser light (L) is irradiated from a window (9) on one side of the light transmitters (4). Moreover, a power supply (15) is connected to the light transmitters (4) through wiring cable (17*a*), and the light transmitters (4) is driven by operating an operation board (not shown) equipped with this power supply (15) to oscillate the laser light (L) to a desired timing. This power supply (15) is settled beside the isolator (2). In addition, although the laser light (L) irradiated from the light transmitters (4) is semiconductor laser light, of course, it is also possible to use laser light source of another kind of light source. Moreover, although the wavelength of the laser light (L) can be chosen suitably, the wavelength of a near infrared light region is adopted in this embodiment of the present invention.

The photo-detector (7) includes a window (8) at one side, which is installed so that the window (8) may be located in the position which faces the laser light (L) irradiated from the above-mentioned light transmitters (4). The photo-detector (7) generates a signal output corresponding to the intensity of the laser light (L) which is detected by this window (8) and displays the measured value on a measured value display part (not shown) of an output unit (16) connected through wiring cable (17*b*). The output unit (16) is disposed beside the isolator (2).

In addition, the construction of the light transmitters (4) and the photo-detector (7) is well-known. Also, the power supply (15) and the output unit (16) may be constructed as a single apparatus. The details of the light transmitters (4) and the photo-detector (7) are omitted since the technology is well-known.

Next, the condensate forming part (3), which is the principal part of this invention, is explained.

Figure 2:
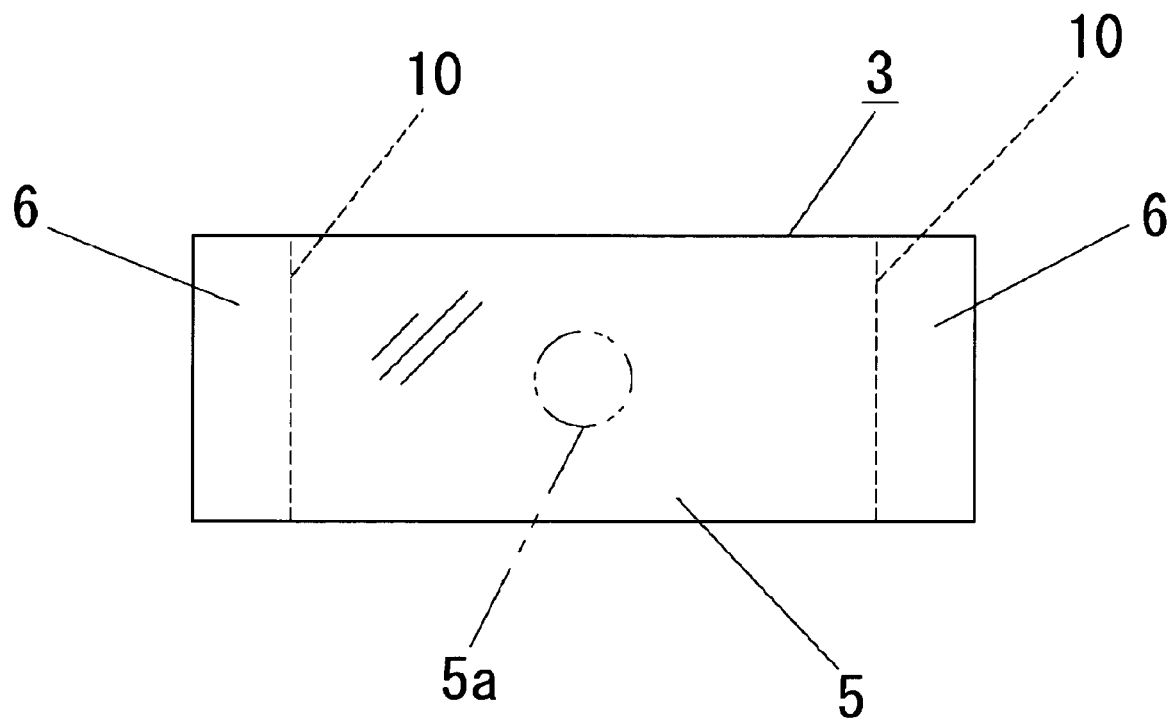
FIG. 2 is a front view of the condensation forming part.
Figure 3:
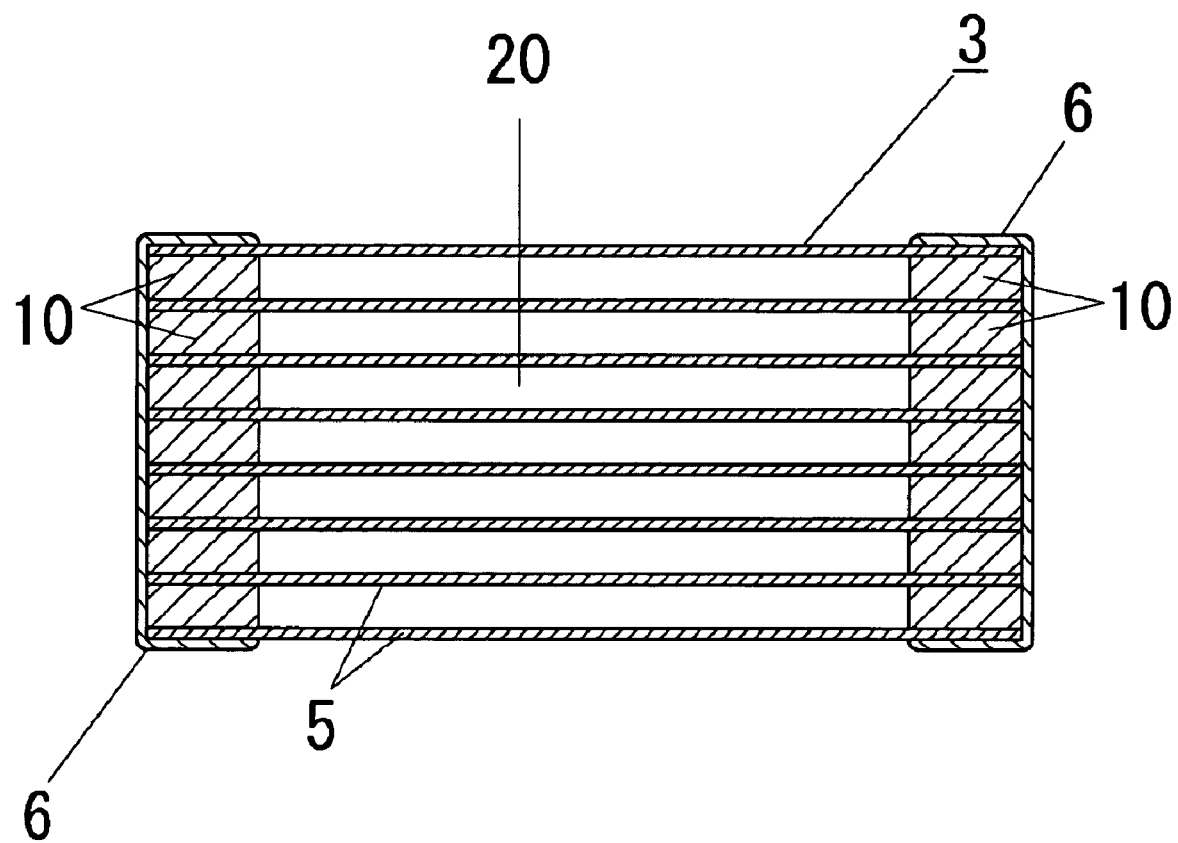
FIG. 3 is a vertical section side view of the condensation forming part.

This condensate forming part (3) is equipped with eight rectangular glass plates (5) (FIG. 2) and arranged so that the direction of a field of the glass plates (5) and each glass plate (5) may be mutually parallel at a respectively fixed interval so that the irradiation direction of the laser light (L) may become almost perpendicular to the field of the glass plates (5). As shown in FIGS. 2 and 3, a supporting element (10) (spacer) of a thin board is installed between the ends of the glass plates (5), respectively. Both ends of each glass plate (5) and each supporting element (10) are fixed together with covering tape (6). Openings (20), excepting the portion covered by the covering tape (6), open to each gap between each glass plate (5) and are formed in an end part of each glass plate (5) where the supporting element (10) is not installed. In this invention, the opening (20) may be formed in the longer end of each glass plate (5). The condensate forming part (3) is arranged so that laser light (L) may be detected at the face of the glass plate (5). In addition, the transparent plate concerning this invention includes the glass plate (5) of this invention and the fixing means of this invention which includes the above-mentioned covering tape (6).

The gap between each glass plate (5) is determined based on the surface form of the sterilization subject (Y) (FIG. 1) in the isolator (2). For example, when the sterilization subject (Y) has a complicated surface form, the condensation forming part (3) is made by narrowing the gaps between the glass plates (5) by using thinner supporting elements (10).

It is hard to narrow the gap between the glass plates (5) of the condensate forming part (3) and to infiltrate hydrogen peroxide gas (X) into the gap between the glass plates (5) through the opening (20). Thus, a cold spot is formed where the hydrogen peroxide gas (X) cannot spread easily. It is possible to correlate approximately the cold spot in the surface of the sterilization subject (Y) and the cold spot in the condensate forming part (3) so that it is possible to presume with sufficient accuracy the condensation situation of the sterilization subject (Y) surface from the condensation information obtained by the condensation sensor (1).

Next, while explaining the operation of the condensation sensor (1), the method of managing the condensation film in the sealed space using this condensation sensor (1) is explained.

At first the intensity of the laser light L, i.e., the standard value of intensity, in a non-condensing state is measured before the injection of hydrogen peroxide gas (X). This is for comparing to the intensity measured in the state of condensation mentioned later.

Next, the hydrogen peroxide gas (X) is injected into the isolator (2). The sterilization subject (Y) and the condensation sensor (1) are installed and decontamination is started inside the isolator (2). Simultaneously, the laser light L is irradiated from the light transmitters (4) continuously or intermittently, and the signal output of the intensity of beam is monitored based on the measured value displayed by the output unit (16). In this working example, this measured value is expressed as the penetration light output of the laser light (L).

Figure 7:
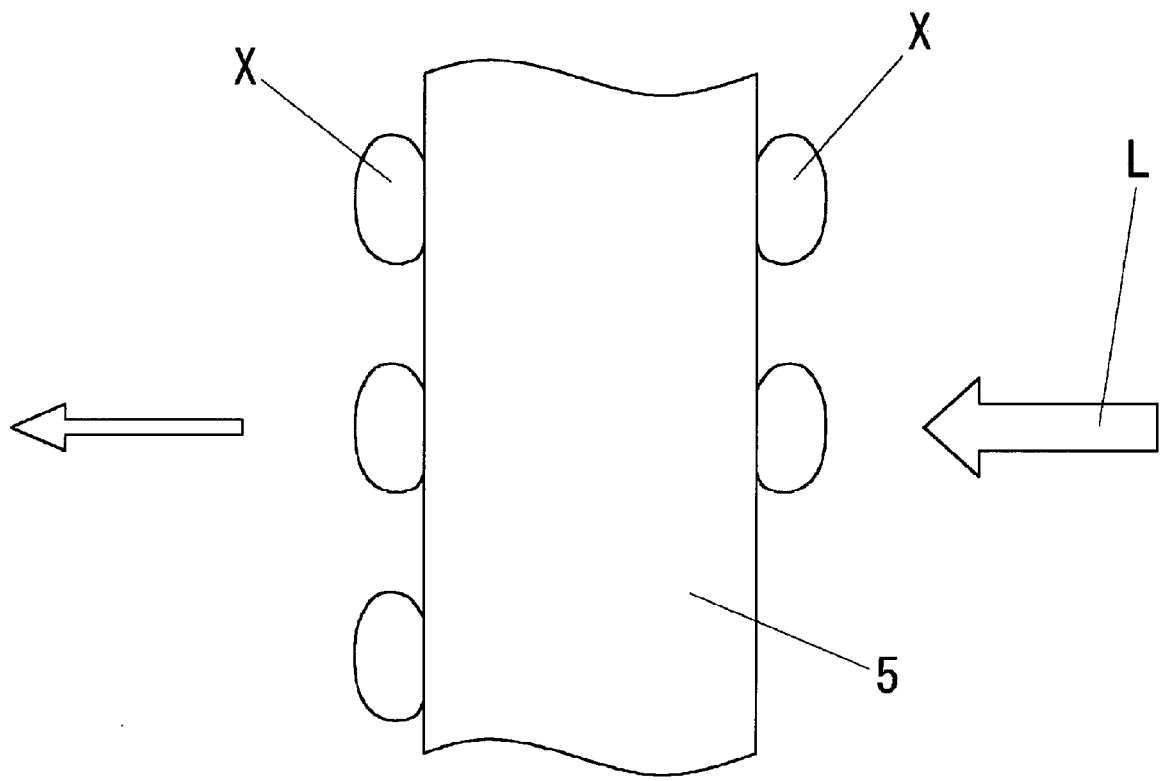
FIG. 7 is an enlarged view showing the hydrogen peroxide gas condensed on the glass window.

Furthermore, if hydrogen peroxide gas (X) continues being supplied, the hydrogen peroxide gas (X) inside the isolator (2) becomes saturated and hydrogen peroxide gas (X) begins to condense on each glass plate (5) of the above-mentioned condensate forming part (3) (FIG. 7).

The intensity of the beam of laser light L in this situation decreases below the above-mentioned standard value of intensity due to the formation of the condensation film on the glass plate (5), and the laser light (L) is scattered about or is absorbed. That is, the measured value of intensity of the beam by the output unit (16) decreases.

When the injection of hydrogen peroxide gas (X) continues, the thickness of the condensation film increases on the plurality of glass plates (5), and the output of the intensity of the beam of laser light L decreases further.

By monitoring the intensity of the beam of laser light L which is detected with the photo-detector (7) before the gas was injected, the initial time of existence of the condensation film in the condensate forming part (3), i.e., a condensation start time, can be determined. It is possible to determine the properties (especially a change in thickness of the film) of a subsequent condensation film. Therefore, the condensation film in a sealed space is manageable by installing the condensation sensor (1) in the sealed space, supplying gas (X) to the sealed space and detecting the existence of the condensation film of the injected gas (X) on the surfaces of the plurality of glass plates (5) by a change of intensity of a beam of laser light L detected by the photo-detector of the condensation sensor (1) with the passing of time.

Next, the condensation sensor (1) of this invention and the experiment result which shows the usefulness of the condensation film management method in the sealed space using the condensation sensor (1) are described.

Figure 8:
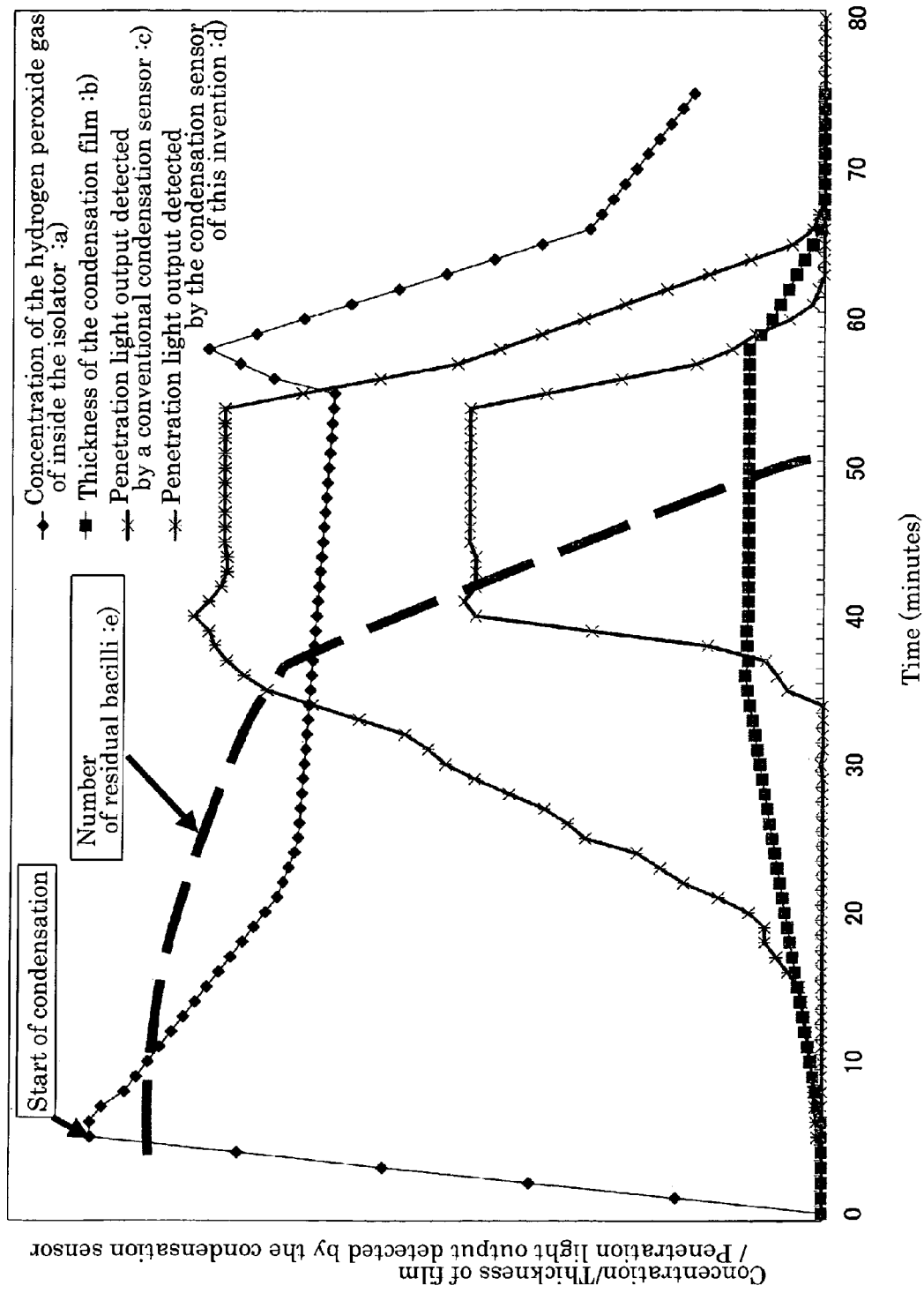
FIG. 8 is the chart showing change of the number of residual bacilli with respect to time.
Figure 12A:
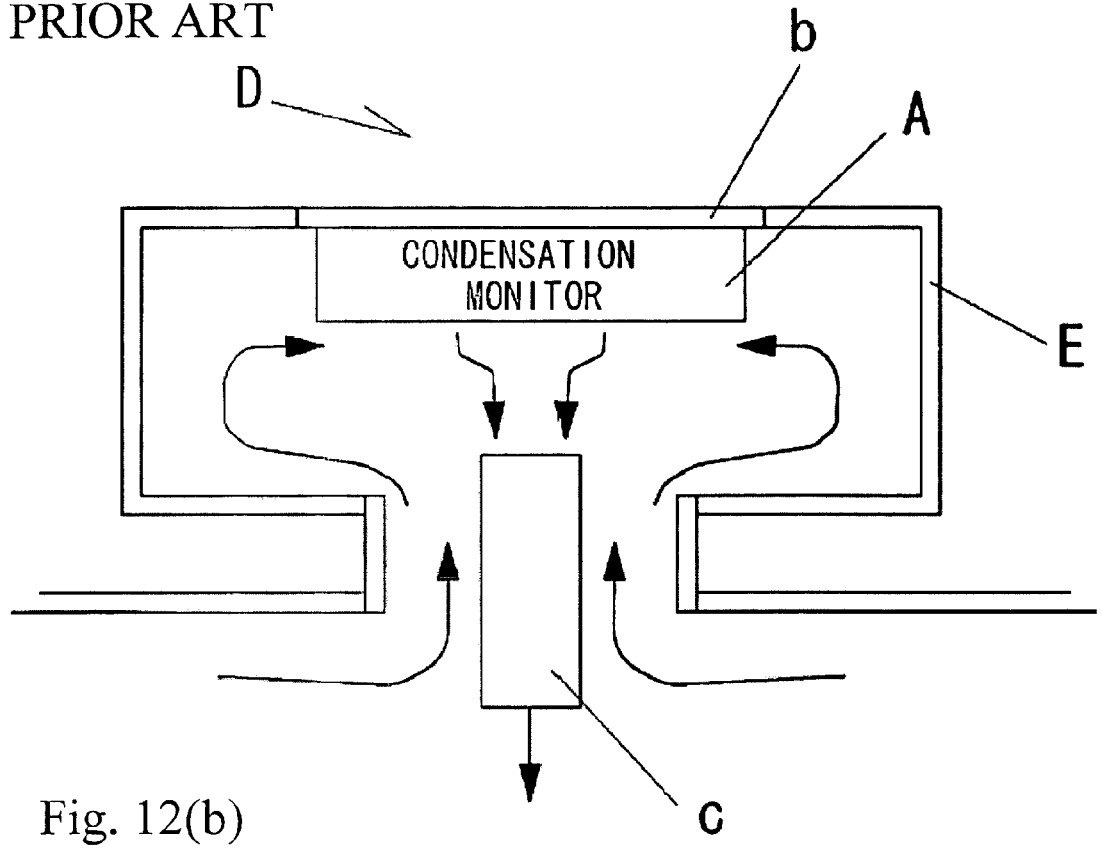
FIG. 12(*a*) is a use mode figure showing the prior art condensation sensor with attached box (E) inside the sealed space.
Figure 12B:
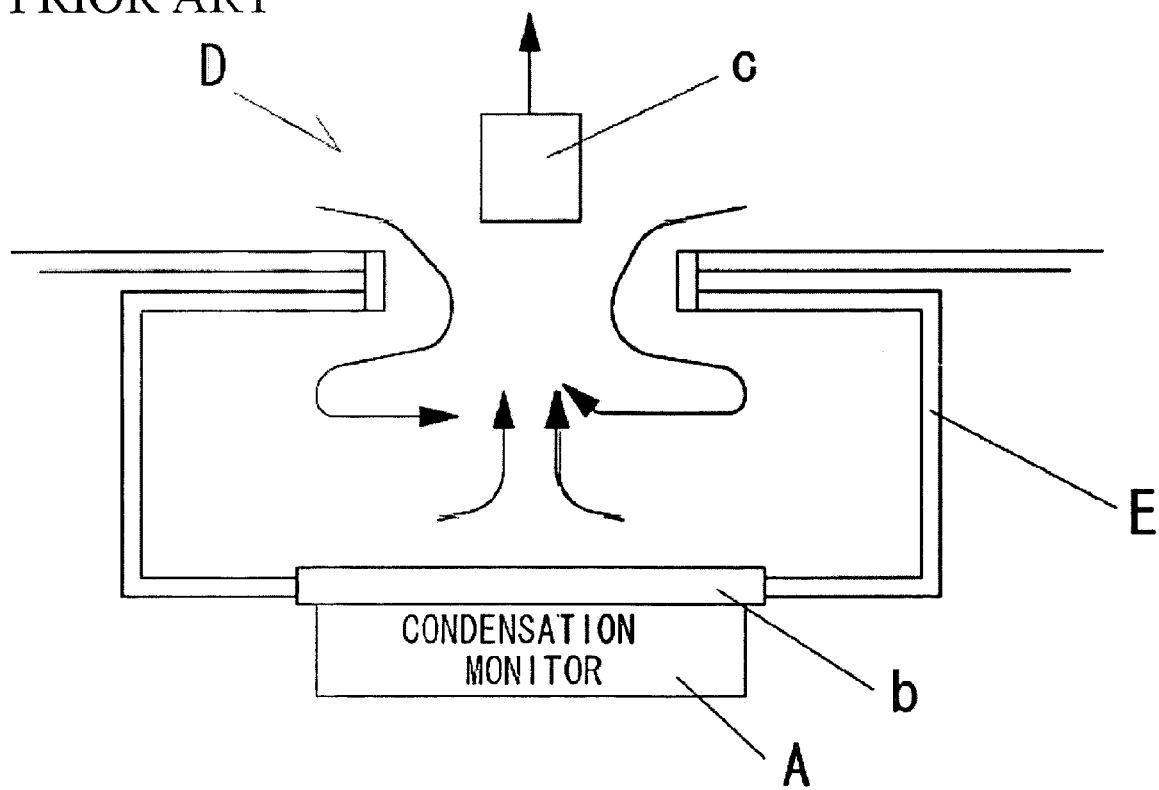

This experiment is conducted in the isolator (2). The condensation sensor (1) of this invention, the conventional condensation sensor (A) (FIGS. 11, 12a, and 12b), a gas sensor to measure the density and a biological indicator to find out the effect of decontamination are installed inside the isolator (2). While supplying hydrogen peroxide gas (X) into the isolator (2), changes of parameters of the supplied hydrogen peroxide gas (X) are recorded. FIG. 8 shows experiment results. These graphs shows a concentration of the hydrogen peroxide gas (X) inside the isolator (2) (mark a), a thickness of the condensation film of the hydrogen peroxide gas (X) condensed in the isolator (2) (mark b), a penetration light output (mark c) detected by the conventional condensation sensor (A), a penetration light output (mark d) detected by the condensation sensor (1) of this invention and a change of the number of residual bacilli (mark e) over time (the horizontal axis is a time axis). The unit or scale of the vertical axis is omitted for convenience. Moreover, the thickness (mark b) of the above-mentioned condensation film is the theoretical value computed from the supplied gas concentration using a predetermined formula. Here, the specific time (t) described below is particular to this experiment, and its value changes by changing experiment conditions, such as gas injection speed, etc.

The reciprocal of the penetration light output is plotted on the graph of FIG. 8 (marks c and d). Therefore, an upward rise in the graph of FIG. 8 (marks c and d) actually indicates that the detected penetration light output decreases with the progression of time, and a downward drop in the graph of FIG. 8 (marks c and d) indicates that the detected penetration light output increases with the progression of time.

After starting to inject the hydrogen peroxide gas (X) into the isolator (2) in this experiment (time t=0), the concentration of hydrogen peroxide gas (X) inside the isolator (2) begins to rise (mark a). Under the conditions of this experiment, the concentration of hydrogen peroxide gas (X) increases linearly in proportion to the lapsed time until about 5 minutes after starting the injection. The concentration of hydrogen peroxide gas (X) begins to decrease gradually just after time t=5 passes. This shows that the gas inside the isolator (2) is nearly in saturation at time t=5, and shows that the hydrogen peroxide gas X begins to condense partly in the isolator (2) simultaneously as the concentration of gas falls.

Therefore, the thickness of the condensation film of hydrogen peroxide gas (X) begins to increase nearly from the time t=5 (mark b), and the thickness of the film increases nearly until time t=35 with an almost fixed inclination.

While the thickness of the condensation film begins to increase, the penetration light output detected by the condensation sensor (1) of this invention begins to decrease. This is because irradiation light is scattered about and absorbed by the condensation film when the condensation film is formed on the plurality of glass plates (5) of the condensate forming part (3). This shows that the condensation sensor (1) of this invention can accurately detect the start time of condensation. The reciprocal of the penetration light output is plotted on the graph of FIG. 8 (mark d) and is shown with an upward rise, i.e., the detected penetration light output decreases with the progression of time.

It is shown that the change of the thickness of the condensation film and of the penetration light output of the condensation sensor (1) with the passage of time, in either graph, is shown with the value increasing as time passes (within the time range of t=5 to near 38). The correlation between the two graphs is found. On the other hand, the penetration light output of the conventional condensation sensor (A) (mark c) shows that, within the time range of about t=0 to nearly 34, the correlation with the thickness of the condensation film is not seen.

Furthermore, each parameter one by one (marks a–d) is considered.

The descending inclination, i.e., reduction, of the concentration of hydrogen peroxide gas (X) (mark a) slows down at the time nearly t=23, increases rapidly at the time nearly t=56 and decreases rapidly after that at time t=59.

Moreover, an increase of the thickness of the condensation film (mark b) stops at the time nearly t=35 and is fixed until the time nearly t=58. Such changes in gas concentration and thickness of film with the passage of time are characteristics particular to activated gas in a sealed space, which shows the characteristics of steam pressure exactly.

Moreover, the penetration light outputs of the condensation sensor (1) and the condensation sensor (A) stop increasing and are almost fixed as the thickness of the condensation film is fixed.

Figure 9:
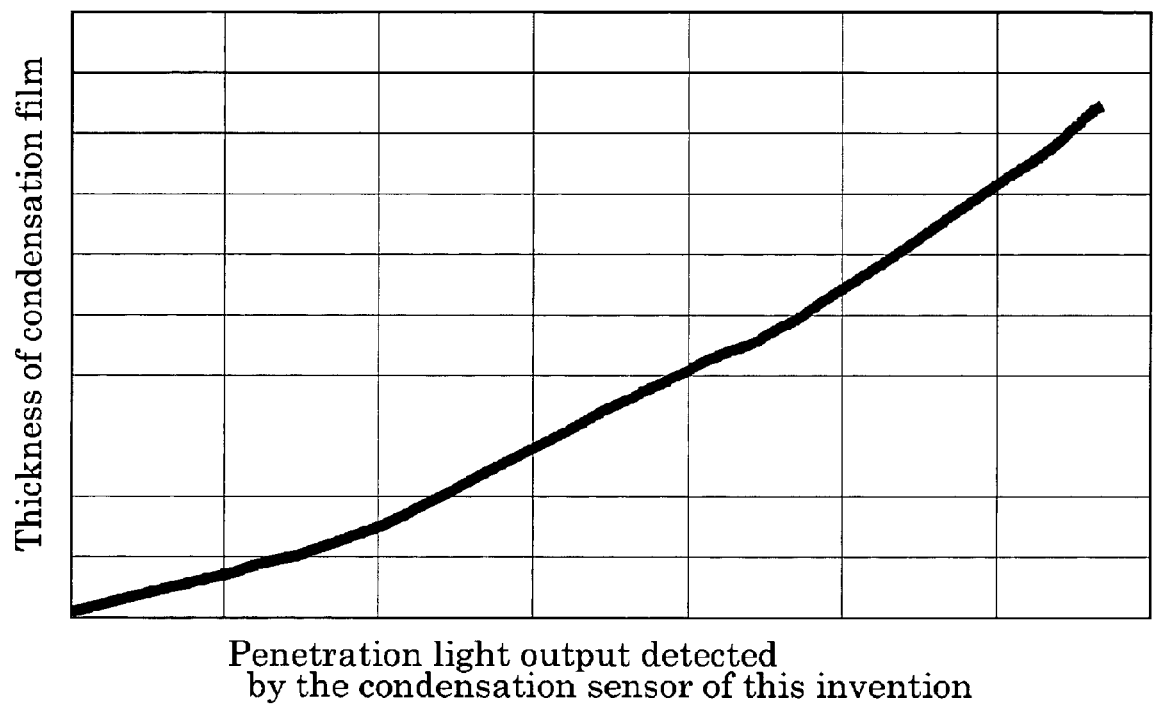
FIG. 9 is the chart showing the relation between the output equivalent of the condensation sensor, and the thickness of a condensation film.

Although it was thought that the condensation sensor (A) (the conventional structure) could detect the start time of condensation of hydrogen peroxide gas (X), this experiment shows the start time of condensation is not detected correctly. The penetration light output starts to decrease only after the thickness of the film is larger than a fixed thickness, which creates a time lag in detection. On the other hand, this experiment shows that the condensation sensor (1) of the present invention correctly detects the start time of condensation and the subsequent increase in thickness of the condensation film. FIG. 9 is a graph illustrating the output of the condensation sensor (1) of this invention on the horizontal axis and the thickness of the condensation film which is computed in the predetermined formula on the vertical axis. FIG. 9 shows that the thickness of the film also increases as the output increases (a penetration light output decreases) and that the penetration light output of the condensation sensor (1) of the present invention and the thickness of the film correlate (proportionally).

Furthermore, a change in the number of residual bacilli in the isolator (2) is considered.

As shown in FIG. 8, the number of residual bacilli (mark e) decreases gradually from time t=0 up to the time nearly t=35 (henceforth "the first reduction region"), then decreases at a higher rate until the number of residual bacilli is 0 near the time t=50 (henceforth "the second reduction region"). The number of residual bacilli is 0 near the time t=50.

When the change in the number of residual bacilli is compared with the change of the thickness of the condensation film, it is shown that the time range (5≦t≦35) when the thickness of the condensation film increases and the time range (0≦t≦35) equivalent to the first reduction region are nearly in agreement and the time range (35≦t≦58) when the thickness is fixed and the time range (35≦t≦58) equivalent to the second reduction region are in nearly agreement. On the other hand, a clear correlation is not seen between the change in the number of residual bacilli and the change in the concentration of hydrogen peroxide gas (X). From the above experimental results, it was shown that the concentration of hydrogen peroxide gas (X) (mark a) and the number of residual bacilli (mark e) of the isolator (2) do not have a clear correlation. On the other hand, there is clear correlation between the thickness of the condensation film (mark b) and the number of residual bacilli (mark e) of the condensation film. This experimental result agrees with the idea that there is a close relationship between the change in the number of residual bacilli of the surface of the decontamination subject in the sealed space after the injection of the gas for decontamination and the condensation of the gas for decontamination. It is also shown that the output of the condensation sensor (1) of this invention and the thickness of the condensation film correlate (FIG. 9), and it is shown that that the condensation sensor (1) of the present invention can detect the start time of condensation and the change in the thickness of the condensation film with sufficient accuracy. On the other hand, as for the conventional condensation sensor (A), it is shown that the start time of condensation cannot be detected correctly and an exact calibration is not made in relation to the thickness of the condensation film.

Figure 10:
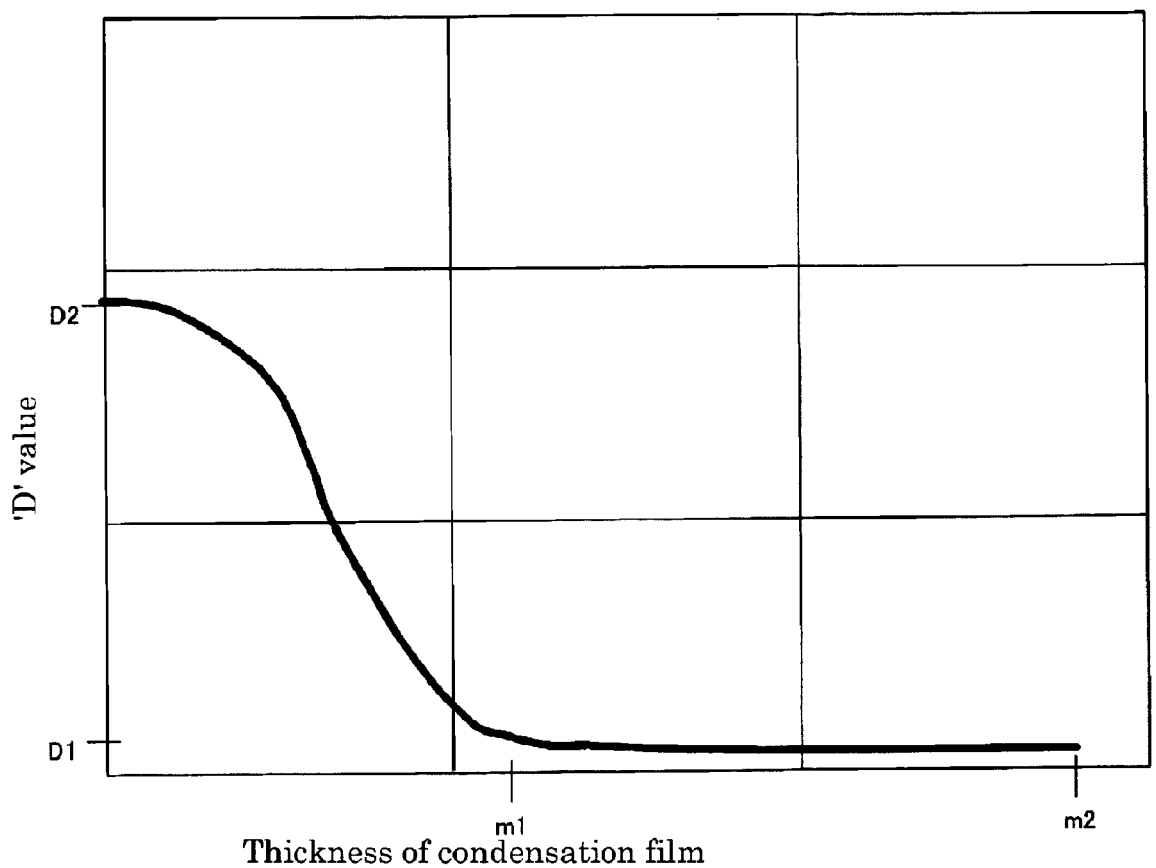
FIG. 10 is the chart showing the relation between thickness of a condensation film, and D value.

Furthermore, there is a fixed relation between the thickness of a condensation film and a D value (the time until the number of residual bacilli becomes 1/10 of the initial number of residual bacilli). The graph shown in FIG. 10 shows the thickness of the condensation film on the horizontal axis and shows the D value on the vertical axis. The thickness of the condensation film increases toward the right-hand side of the graph along the horizontal axis, and on the other hand, the D value increases upward along the vertical axis and the sterilization effect lowers.

By explaining the relationship between the thickness of the condensation film and the D value according to FIG. 10, a clear correlation is seen between the thickness of the film and the D value in the range of the graph as the D value is reduced mostly proportionally (from D2 to D1) in the region of condensation film thickness from 0 to m1. That is, the sterilization effect improves so that the thickness of the condensation film increases. On the other hand, in the range of condensation film thickness from m1 to m2, the D value is fixed at D1. That is, even if the injection of hydrogen peroxide gas (X) continues and the thickness of the condensation film increases in this range, the sterilization effect does not improve. Therefore, once the thickness of the predetermined value is formed, it is not necessary to continue supplying hydrogen peroxide gas (X).

Then, it is very important to detect correctly the predetermined thickness at which improvement in the above sterilization effects becomes fixed so that hydrogen peroxide gas (X) is not supplied superfluously during sterilization. In order to detect this predetermined thickness, the sensor for detecting a change in the thickness of the condensation film in detail and for detecting a minute thickness is needed. It is possible to solve his problem by using the condensation sensor (1) of the present invention described. Thus, by detecting the change in the thickness of the condensation film based on the change in the intensity of the beam detected by the photo-detector (7) of the condensation sensor (1), the quantity of hydrogen peroxide gas (X) which should be supplied can be determined. In addition, problems like time lag arise in the detection at the start time of condensation by the conventional condensation sensor (A), and therefore, exact detection using the conventional condensation sensor (A) is difficult.

In addition, the number of glass plates (5), the thickness of each glass plate and a gap between the plates in the condensation sensor (1) of the present invention may be suitably changed according to the size and shape of the sterilization subject (Y). Furthermore, the plate arbitrarily can have a square shape, a round shape, a trapezoidal shape, etc., without being restricted to the shape of the above-mentioned rectangle. Moreover, it is possible to use a transparent plate of a transparent resin material instead of the glass plate (5). Moreover, the size of the glass plate (5) is preferably more than the diameter (about 1 mm) of a beam of the laser light L. While it is sufficient that a dimension of the glass plate (5) is at least equal to the diameter of the beam and it is sufficient that the thickness (0.5 mm or less) of the glass plate (5) is at least the thickness to which gas can condense onto the plate, the condensation sensor (1) can be constructed conventionally smaller as compared with structure as a whole.

Moreover, the fixing means for fixing each glass plate 5 and the supporting element (10) is not only the method of fixing the above-mentioned covering tape (6) but also the composition which fixes the plurality of glass plates (5) and the supporting elements (10) by adhesive material.

Figure 4:
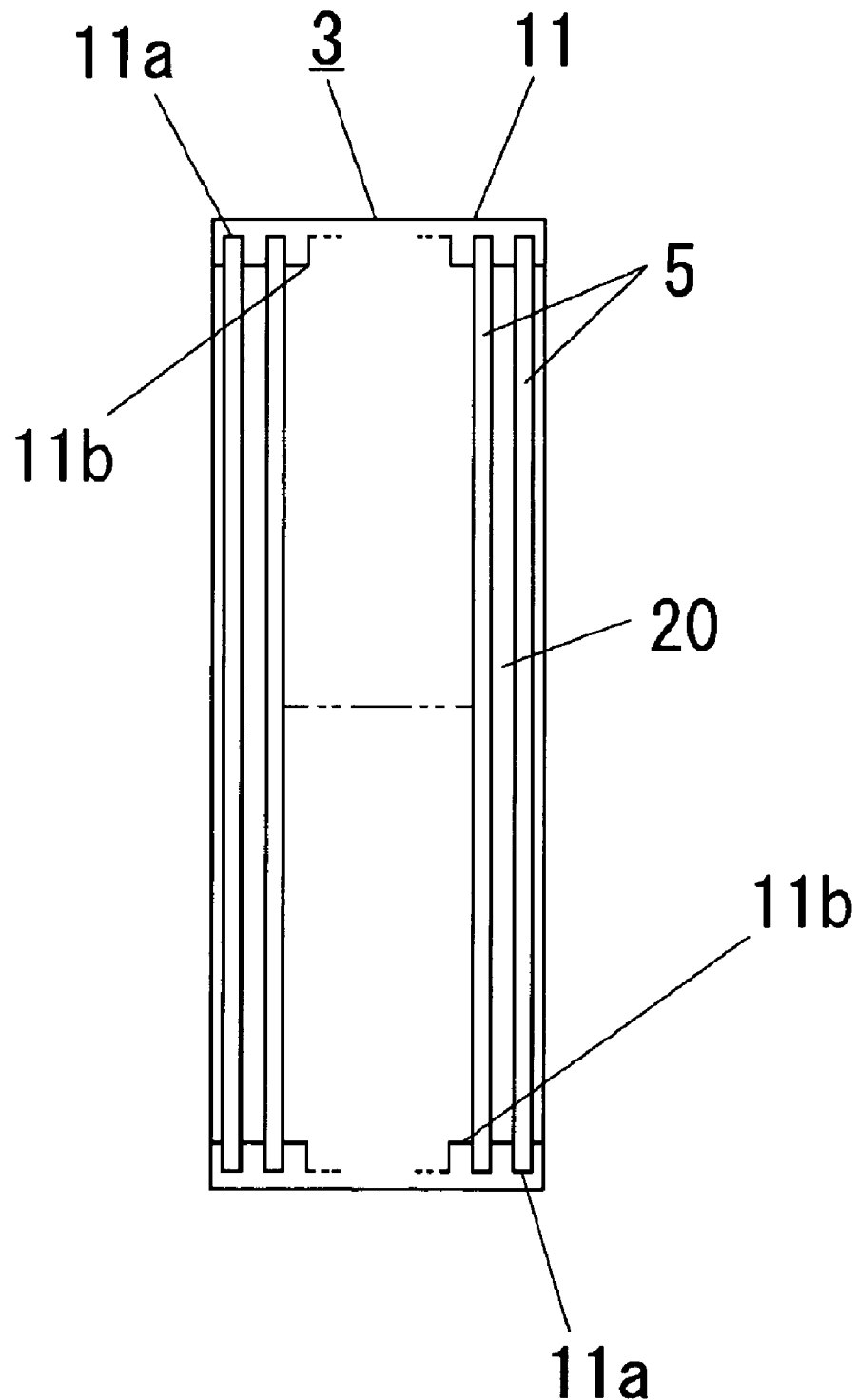
FIG. 4 is a plane view of the condensation forming part with a maintenance implement.
Figure 5:
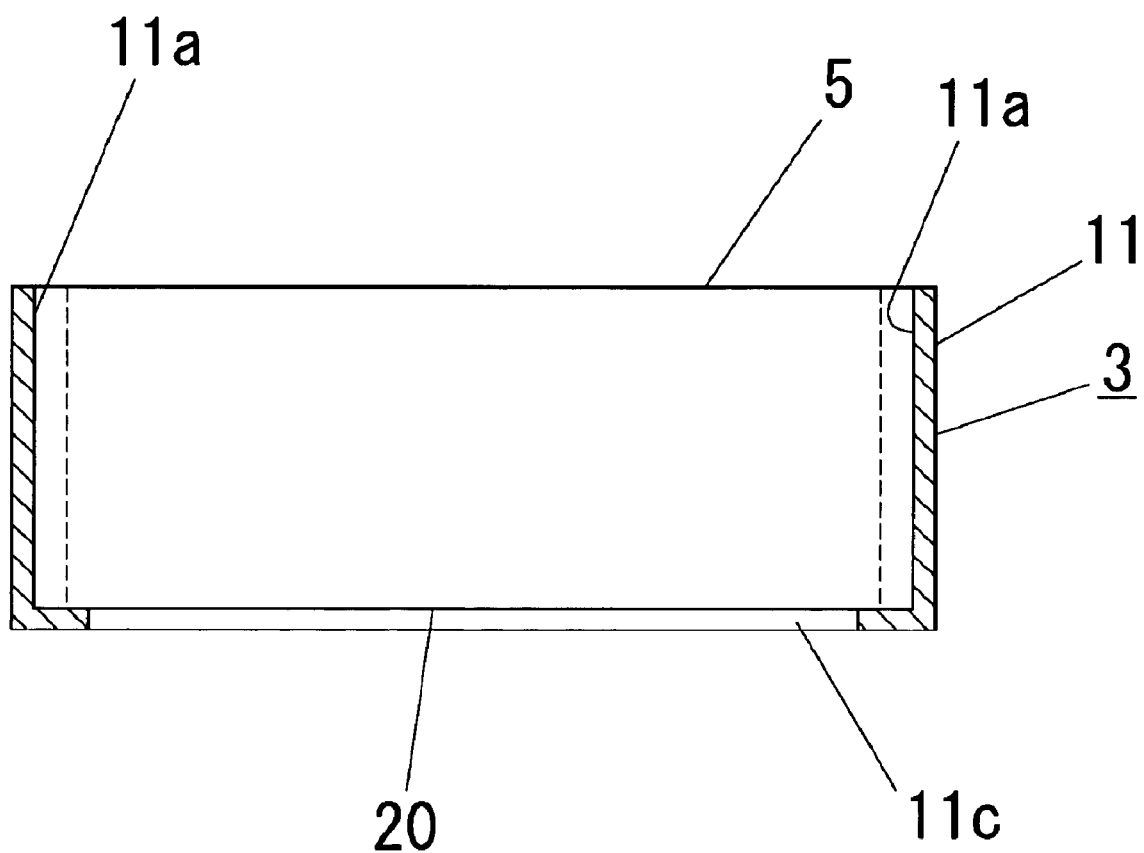
FIG. 5 is a vertical section side view of the condensation forming part with the maintenance implement.

It is also preferable that, as shown in FIGS. 4 and 5, the opening of the condensate forming part (3) is formed so that the insertion of the glass plates (5) may be attained by joining the upper part of the glass plates (5) and a supporting implement (11) in the shape of a box equipped with an inner surface including walls (11b) which face each other. As for this supporting implement (11), two or more holding slots (11a) are formed in the perpendicular direction at the surface of the wall (11b) and (11b) within the above. The upper and lower ends of the glass plate (5) are inserted into the respective holding slots (11a), and the glass plates (5) are parallel. The opening (20) is formed in a portion (namely, the upper surface side) of the end where the supporting implement (11) are absent from the condensate forming part (3), and the opening (20) is formed for hydrogen peroxide gas (X) to infiltrate into this gap between the glass plates (5). In addition, the opening (20) is formed in the center of the undersurface of the supporting implement (11) as shown in FIG. 5 to open the gap between the glass boards (5).

Moreover, in this structure, as a suitable number of glass plates (5) are inserted in the holding slots (11a), the gap interval between the glass boards (5) can be adjusted suitably. In addition, the present invention provides a holding side of the wall (11b) in which the holding slot (11a) is formed in an inner surface thereon.

Figure 6:
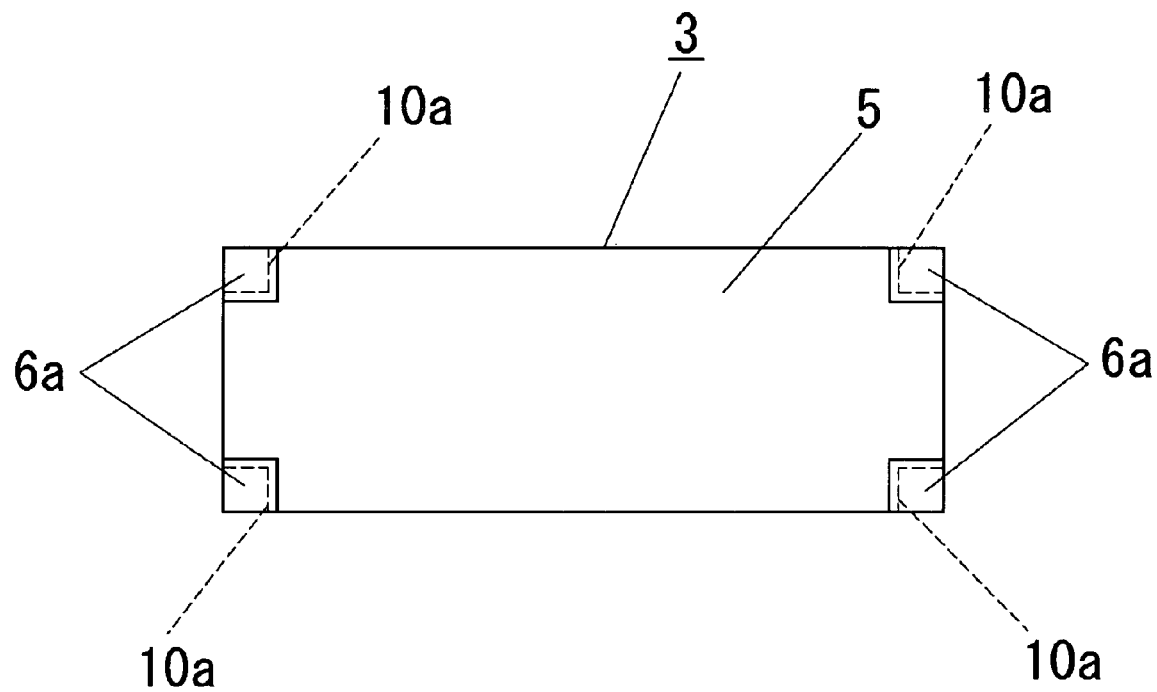
FIG. 6 is a front view of the condensation forming part concerning other examples of an enforcement form.

As shown in FIG. 6, supports (1a) having sides which are each shorter than the respective sides of the glass plate (5) are disposed on four corners of the glass plate (5). At least a portion of these corner parts are covered by covering tape (6a) to fix the glass plate (5) and supports (10a) collectively to prevent separation. Since the gap between the glass plates (5) is open in four directions by the openings (20) except where the covered portions are located, breathing is improved to allow the hydrogen peroxide gas (X) to permeate easily.

Furthermore, the direction of the surface of the glass plate (5) and the irradiation of the laser light (L) may not be perpendicular or parallel. In one embodiment of the present invention, the direction of the surface of the glass plate (5) is positioned 45 degrees in the irradiation direction. Then, it becomes possible to increase the intensity of the beam according to the amount of the change in the thickness of the film as compared to the above-mentioned structure, in which the beam is perpendicular, and it becomes possible to raise the sensitivity of the photo-detector.

Moreover, in the condensation sensor (1) of the present invention, the laser light (L) is suitable to be irradiated at a central region (5a) of the glass plate (5), as shown in FIG. 2, where the progress of sterilization is slowest on the glass plate (5). Then, it is possible to prevent the imperfect decontamination of the subject (Y). Alternatively, it is possible that the condensate forming part (3) can be moved along the direction of a face of the glass plate (5) from the outside of the isolator (2) and the laser light (L) may be irradiated to a requested region of the surface of the glass plate (5).

Figure 13:
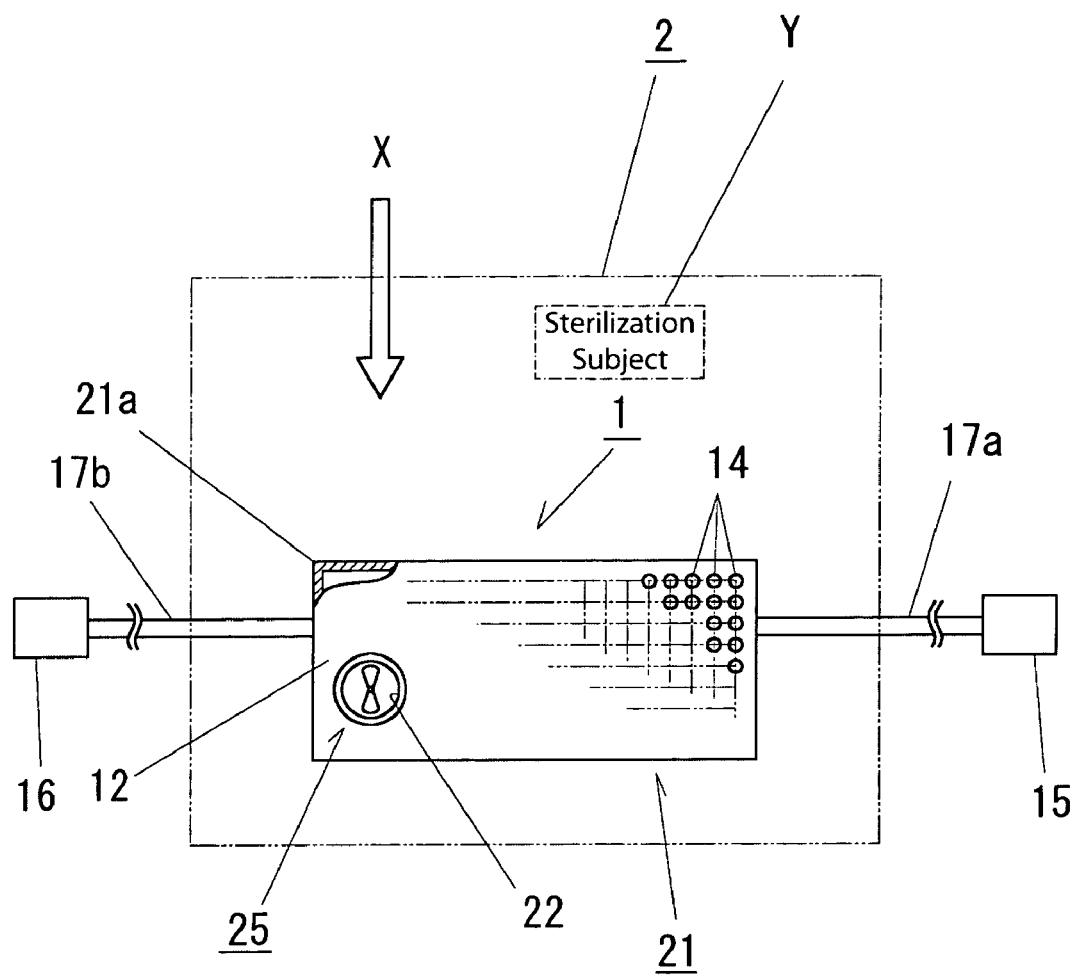
FIG. 13 is a partial sectional view of an embodiment of the condensation sensors contained in a porous case with two or more holes of the porous case.
Figure 14:
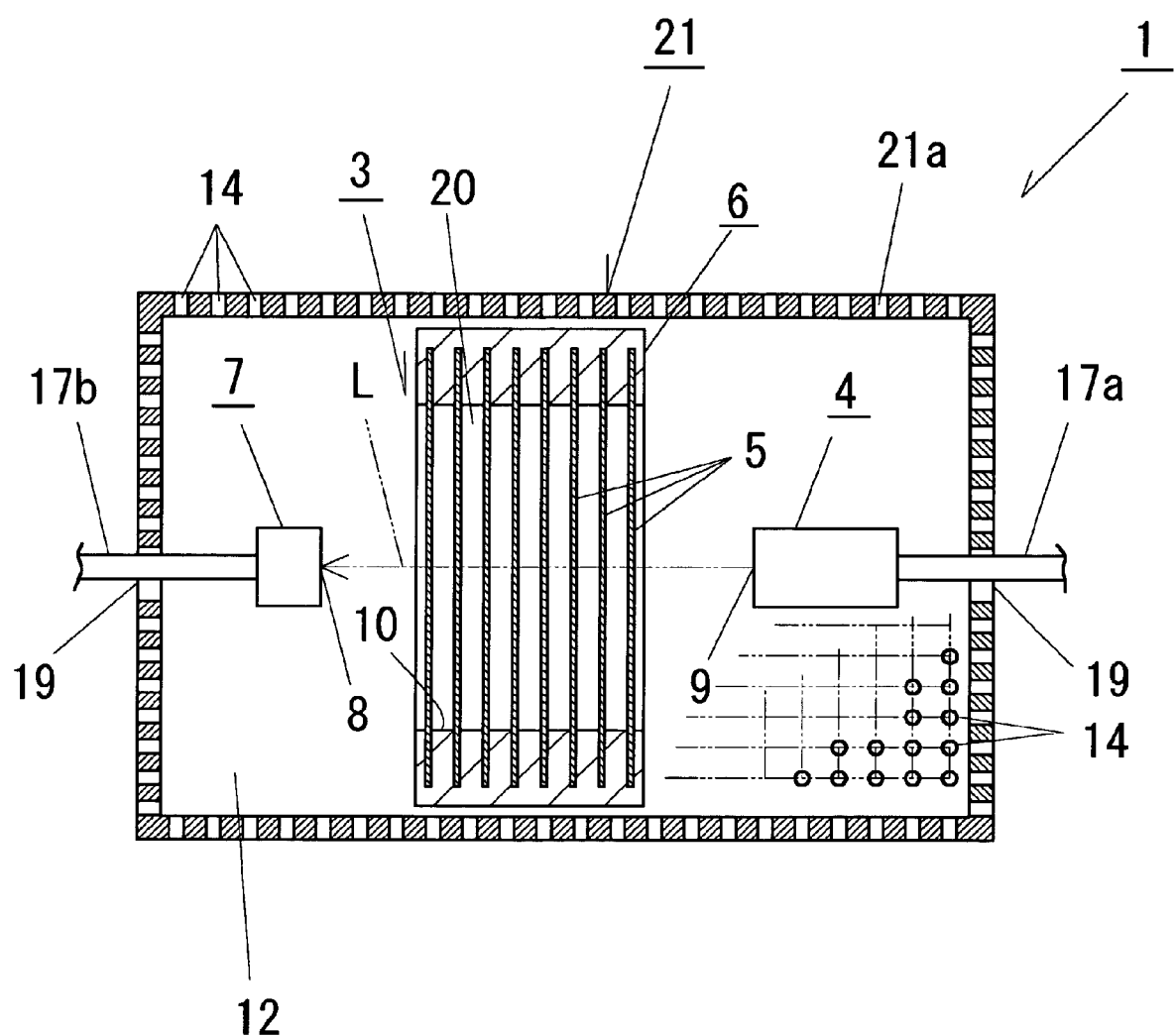
FIG. 14 is a partial expansion transverse cross section of the porous case.
Figure 15:
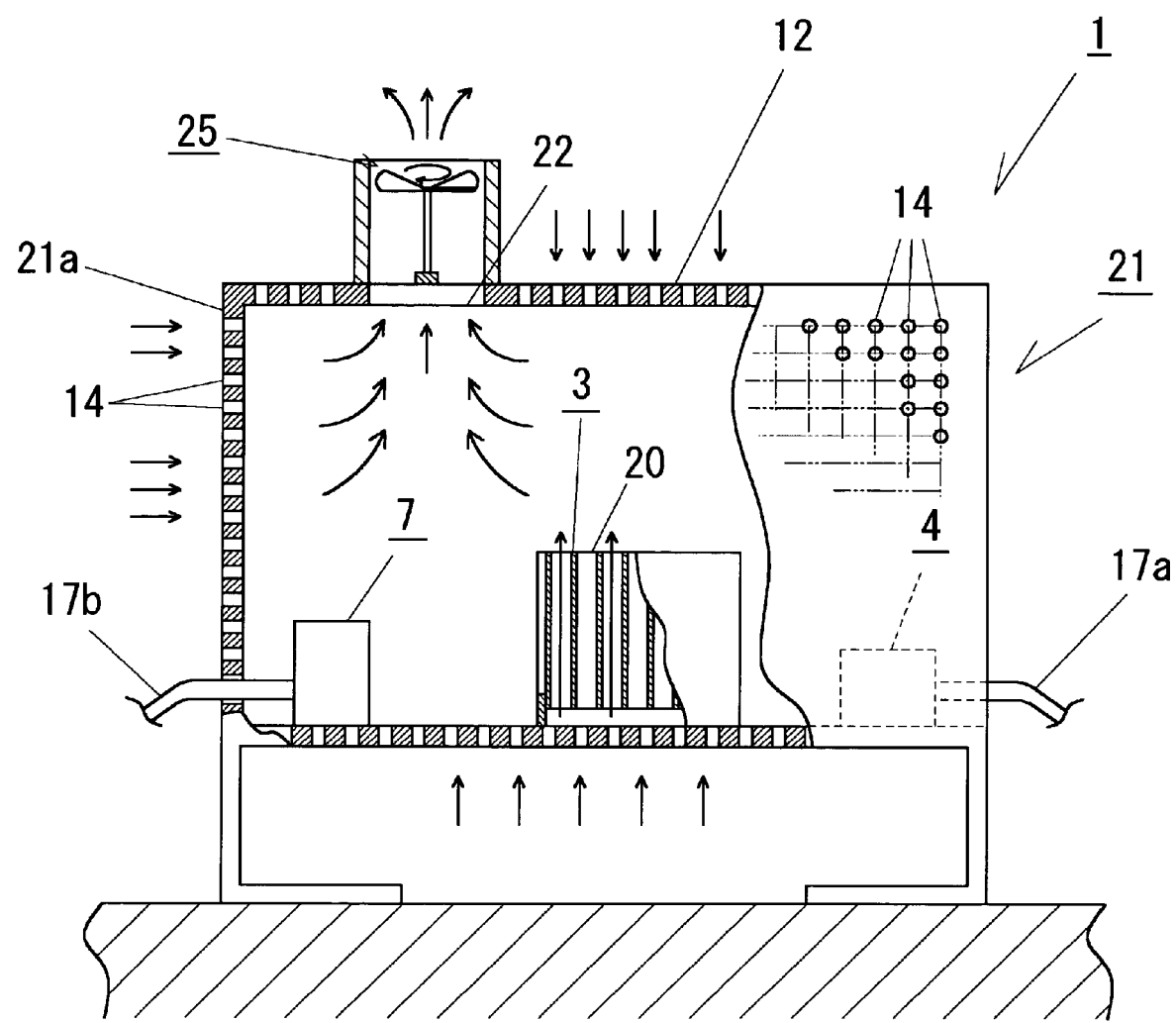
FIG. 15 is a partial sectional view of the porous case.

Alternatively, the structure of the condensation sensor mentioned above comprising the light transmitters (4), the photo-detector (7) and the condensate forming part (3) may be contained in a porous case (21) formed with holes (14) in the surface thereof for introducing air, as shown in FIG. 13. The wiring cables (17a, 17b) enter through openings (19) in the porous case (21) to connect to the light transmitters (4) and the photo-detector (7), respectively, as shown in FIG. 14. Specifically, the condensate forming part (3) is fixed in the porous case (21). In this example, an SUS punching board (21a) is used for constructing the porous case (21).

Therefore, the holes (14) for introducing air from the inside the isolator (2) are formed in most of the porous case (21). In the ceiling part (12) of the porous case (21), a duct (22) for exhausting the gas inside the porous case (21) is arranged. A ventilation fan (25) is settled in the duct (22). When the ventilation fan (25) is driven, the air in the isolator (2), which contains hydrogen peroxide gas (X), is introduced into the porous case (21) through the holes (14) and the air introduced in the porous case (21) is exhausted into the isolator (2) through the duct (22).

A breathable material, such as Tyvek sheet, may surround the condensate forming part (3) or the condensation sensor (1) itself instead of the porous case (21).

In addition, two or more condensation sensors (1) of this invention may be disposed in multiple locations in the sealed space, thereby allowing stricter management of the condensation gas in the sealed space. Moreover, it is then possible to prepare beforehand two or more different condensate forming parts to exchange promptly to correspond suitably to the sterilization subject of various shapes and sizes. Furthermore, in this working example, the intensity of the beam can be monitored not only with a penetration light output but also with other outputs, such as the rate of transmission.

Moreover, although the structure described above decontaminates an inside of the sealed space using hydrogen peroxide gas (X), according to an embodiment of this invention, other gases can be used for decontamination. In addition, the gas for sterilization may be contained in the gas for decontamination. Furthermore, it is possible to apply this invention in order to detect the condensation state of an activated gas. The laser light (L) is suitable for the light irradiated from the light transmitters (4) because it is a powerful and coherent narrow beam, but other light sources, such as an LED (Light Emitting Diode) or another light source may be usable. Further, the condensation sensor (1) of this invention may be installed inside a path box, inside a room, etc., and detects the condensation state of the hydrogen peroxide gas (X) inside this contained space.

Having described embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A condensation sensor comprising:

at least one light transmitters configured to irradiate light in an irradiating direction from a light source;

at least one photo-detector disposed to face the irradiated light of the light transmitters and configured to generate a signal output corresponding to an intensity of a beam of the irradiated light; and a condensate forming part including at least one transparent plate positioned between the light transmitters and the photo-detector so that the irradiated light is directed on a surface of the transparent plate on which a gas, when introduced to surround the transparent plate, condenses and forms a condensation film, wherein the condensation sensor is configured to detect forming of the condensation film on the surface of the transparent plate, based on a change in a time-course in the intensity of the beam of the irradiated light detected at the photo-detector through the condensation film on the transparent plate, the condensate forming part comprises a spacer formed from a thin plate and installed so that at least a portion thereof is fixed between a pair of the transparent plates, and a fixing unit fixing the spacer and the transparent plates, and the transparent plates forms a passage through which air flows between each gap formed by the transparent plates.

2. A condensation sensor according to claim 1, wherein the transparent plate of the condensate forming part is arranged so that a direction of a face of the transparent plate and the irradiation direction between the light transmitters and the photo-detector are substantially perpendicular.

3. A condensation sensor according to claim 1, wherein the light transmitters is a laser light.

4. A condensation sensor according to claim 1, wherein the light transmitters is a LED.

5. A condensation sensor comprising:
at least one light transmitters configured to irradiate light in an irradiating direction from a light source;
at least one photo-detector disposed to face the irradiated light of the light transmitters and configured to generate a signal output corresponding to an intensity of a beam of the irradiated light; and
a condensate forming part including at least one transparent plate positioned between the light transmitters and the photo-detector so that the irradiated light is directed on a surface of the transparent plate on which a gas, when introduced to surround the transparent plate, condenses and forms a condensation film, wherein
the condensation sensor is configured to detect forming of the condensation film on the surface of the transparent plate, based on a change in a time-course in the intensity of the beam of the irradiated light detected at the photo-detector through the condensation film on the transparent plate,
at least two of the transparent plates are substantially in parallel with a fixed gaps,
the condensate forming part has a supporting implement including two or more maintenance slots each of which supports an end of the transparent plate, and
the at least two of the transparent plates are held in parallel to each other to insert the end of the transparent plate into the maintenance slot to form an opening which allows air to flow between each of the gaps between the transparent plates.

6. A condensation sensor according to claim 5, wherein the transparent plate of the condensate forming part is arranged so that a direction of a face of the transparent plate and the irradiation direction between the light transmitters and the photo-detector are substantially perpendicular.

7. A condensation sensor according to claim 5, wherein the light transmitters is a laser light.

8. A condensation sensor according to claim 5, wherein the light transmitters is a LED.

9. A condensation sensor comprising:
at least one light transmitters configured to irradiate light in an irradiating direction from a light source;
at least one photo-detector disposed to face the irradiated light of the light transmitters and configured to generate a signal output corresponding to an intensity of a beam of the irradiated light; and
a condensate forming part including at least one transparent plate positioned between the light transmitters and the photo-detector so that the irradiated light is directed on a surface of the transparent plate on which a gas, when introduced to surround the transparent plate, condenses and forms a condensation film, wherein
the condensation sensor is configured to detect forming of the condensation film on the surface of the transparent plate, based on a change in a time-course in the intensity of the beam of the irradiated light detected at the photo-detector through the condensation film on the transparent plate, and
at least one of the condensate forming part and the condensation sensor is surrounded with a breathable material.

10. A condensation sensor according to claim 9, wherein the transparent plate of the condensate forming part is arranged so that a direction of a face of the transparent plate and the irradiation direction between the light transmitters and the photo-detector are substantially perpendicular.

11. A condensation sensor according to claim 9, wherein the light transmitters is a laser light.

12. A condensation sensor according to claim 9, wherein the light transmitters is a LED.

13. A condensation sensor comprising:
at least one light transmitters configured to irradiate light in an irradiating direction from a light source;
at least one photo-detector disposed to face the irradiated light of the light transmitters and configured to generate a signal output corresponding to an intensity of a beam of the irradiated light; and
a condensate forming part including at least one transparent plate positioned between the light transmitters and the photo-detector so that the irradiated light is directed on a surface of the transparent plate on which a gas, when introduced to surround the transparent plate, condenses and forms a condensation film, wherein
the condensation sensor is configured to detect forming of the condensation film on the surface of the transparent plate, based on a change in a time-course in the intensity of the beam of the irradiated light detected at the photo-detector through the condensation film on the transparent plate, and
at least one of the condensate forming part and the condensation sensor is contained in a porous case comprising an outlet, at least two holes passing through a wall of the porous case, and air inhalation equipment so that airflow is created by introducing air into the holes in the porous case and discharging the air through the outlet.

14. A condensation sensor according to claim 13, wherein the transparent plate of the condensate forming part is arranged so that a direction of a face of the transparent plate and the irradiation direction between the light transmitters and the photo-detector are substantially perpendicular.

15. A condensation sensor according to claim 13, wherein the light transmitters is a laser light.

16. A condensation sensor according to claim 13, wherein the light transmitters is a LED.

17. A method for managing a condensation film in a sealed space using at least one condensation sensor comprising the steps of:
providing in a sealed space at least one condensation sensor having a light transmitter, a photo-detector, and a transparent plate positioned between the light transmitter and the photo-detector;
supplying a gas to the sealed space;
irradiating a beam of light from the light transmitter toward the photo-detector through the transparent plate on which surface a condensation film is formed when the gas condenses;

detecting a forming of a condensation film on the transparent plate, based on a change in a time-course in intensity of the beam detected at the photo-detector through the condensation film of the transparent; and detecting a change of thickness of the condensation film formed on the transparent plate when the gas condenses, using the change of the intensity of the beam detected in the detecting step.

18. A method of managing a condensation film in a sealed space using a condensation sensor according to claim 17, wherein the gas supplied to the sealed space is a gas for decontamination.

19. A method for managing a condensation film in a sealed space using a condensation sensor according to claim 18, wherein the gas for decontamination is a hydrogen peroxide gas.

20. A method of managing a condensation film in a sealed space using a condensation sensor according to claim 17, wherein, in the step of providing, the at least one condensation sensor includes at least two condensation sensors in the sealed space.

* * * * *